(12) United States Patent
Tehrani et al.

(10) Patent No.: US 12,185,977 B2
(45) Date of Patent: Jan. 7, 2025

(54) DEVICE, A SYSTEM, AND A METHOD FOR ACCESS CANNULA ADVANCEMENT

(71) Applicant: BOSTON SCIENTIFIC SCIMED, INC., Maple Grove, MN (US)

(72) Inventors: Ramin N. Tehrani, Jamaica Plain, MA (US); Christopher A. Benning, Hopkinton, MA (US); Gregory Thomas Hughes, Hanson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/518,139

(22) Filed: Nov. 22, 2023

(65) Prior Publication Data

US 2024/0090920 A1 Mar. 21, 2024

Related U.S. Application Data

(63) Continuation of application No. 17/249,057, filed on Feb. 18, 2021, now Pat. No. 11,871,962.

(60) Provisional application No. 62/987,740, filed on Mar. 10, 2020.

(51) Int. Cl.
*A61B 17/34* (2006.01)
*A61B 17/00* (2006.01)

(52) U.S. Cl.
CPC .... *A61B 17/3423* (2013.01); *A61B 17/00234* (2013.01); *A61B 2017/00296* (2013.01)

(58) Field of Classification Search
CPC .......... A61B 17/3423; A61B 17/00234; A61B 2017/00296
See application file for complete search history.

(56) References Cited

U.S. PATENT DOCUMENTS

| 2010/0048990 A1* | 2/2010 | Bakos ................ A61B 17/3478 604/103.05 |
| 2012/0316584 A1* | 12/2012 | Miles ............... A61B 17/12122 606/157 |
| 2017/0319232 A1* | 11/2017 | Kiev .................. A61B 17/3415 |

* cited by examiner

*Primary Examiner* — Shaun L David
*Assistant Examiner* — Rachael L Geiger
(74) *Attorney, Agent, or Firm* — Fay Kaplun & Marcin, LLP (57) ABSTRACT

A device includes an access cannula, a puncturing element, a handle. The access cannula includes a lumen extending therethrough. The access cannula is sized and shaped to extend through an endoscopic shaft to a target tissue within a living body. The puncturing element is sized and shaped to extend through the lumen of the access cannula and distally out a distal end of the access cannula. The handle includes a handle body and a mechanism for advancing the access cannula from a proximal position relative to the puncturing element, where a puncturing tip of the puncturing element is exposed distal to a distal end of the access cannula, to a distal position relative to the puncturing element, where the distal end of the access cannula covers the puncturing tip of the puncturing element.

12 Claims, 8 Drawing Sheets

DEVICE, A SYSTEM, AND A METHOD FOR ACCESS CANNULA ADVANCEMENT

PRIORITY CLAIM

The present application is a Continuation of U.S. patent application Ser. No. 17/249,057 filed on Feb. 18, 2021; which claims priority to U.S. Provisional Patent Application Ser. No. 62/987,740 filed Mar. 10, 2020. The disclosures of the above application(s)/patent(s) are incorporated herewith by reference.

FIELD

The present disclosure relates to endoscopic ultrasound (EUS) access devices, systems, and method for accessing anatomical structures (e.g., the pancreatico-biliary tree).

BACKGROUND

Endoscopic ultrasound (EUS) access procedures, i.e., access procedures performed under ultrasound guidance, may be used to access anatomical structures such as the pancreatico-biliary tree or the liver. A pancreatico-biliary access procedure, such as, for example, a procedure to penetrate a biliary duct to insert a stent and bypass a blockage, may differ from other types of access procedures in that the target anatomy is exceedingly narrow. Many EUS access devices are not sufficiently maneuverable for such procedures and, even when sufficiently maneuverable, may be subject to other difficulties. For example, a long, thin sharp may easily make an initial puncture hole, but a risk exists of extending the sharp too far so that the sharp passes through the entire thickness of the bile duct to pass out of the duct into other non-targeted tissue creating an undesired opening in the bile duct.

Additionally, if an access cannula is not inserted sufficiently deeply in the anatomical structure prior to withdrawing the sharp, the access cannula may be left outside the structure after the sharp is withdrawn. Thus, it is important for the clinician to attain a correct depth of puncture. It is sometimes difficult for the clinician to assess the depth of penetration as it may be difficult for the clinician to identify a transition point between the sharp and the access cannula under EUS and/or fluoroscopy to confirm that the access cannula has inserted in the structure to a proper depth.

SUMMARY

The present disclosure relates to a device which includes an access cannula, a puncturing element, and a handle. The access cannula includes a lumen extending therethrough. The access cannula is sized and shaped to extend through an endoscopic shaft to a target tissue within a living body. The puncturing element is sized and shaped to extend through the lumen of the access cannula and distally out a distal end of the access cannula. The handle includes a handle body and a mechanism for advancing the access cannula from a proximal position relative to the puncturing element, where a puncturing tip of the puncturing element is exposed distal to a distal end of the access cannula, to a distal position relative to the puncturing element, where the distal end of the access cannula covers the puncturing tip of the puncturing element.

In an embodiment, in the proximal position, the puncturing tip extends a first predetermined distance relative to the distal end of the access cannula and, when the advancement mechanism is actuated, the access cannula advances at least the first predetermined distance relative to the puncturing element.

In an embodiment, the device further includes a rotation hub fixed to the access cannula and coupled to a proximal end of the handle body, the rotation hub being rotatable relative to the handle body and slidable a second predetermined distance relative to the handle body; and a cap fixed to the puncturing element and couplable to the rotation hub wherein, when the cap and the rotation hub are coupled, the puncturing tip extends the first predetermined distance relative to the distal end of the access cannula.

In an embodiment, the proximal end of the handle includes an end cap into which a distal portion of the rotation hub is inserted to couple the rotation hub to the handle, the end cap having a seat against which a first spring is positioned.

In an embodiment, the rotation hub includes a first proximal flange and a second distal flange with a shaft extending therebetween, the shaft having a washer and a second spring slidable thereover and constrained between the first and second flanges.

In an embodiment, the end cap further includes deformable tabs at a proximal end thereof that allow insertion of the washer therein and resist retraction of the washer thereout so that, when the rotation hub is inserted into the end cap, the washer is positioned against the first spring at a distal end and against the deformable tabs at a proximal end.

In an embodiment, the cap has a distal portion sized and shaped to cover a proximal portion of the rotation hub and two wings attached thereto, each wing having a tab extending radially inward off of a distal end of the wing.

In an embodiment, when the cap is advanced over the rotation hub, the tabs extending off the wings lock onto the first flange of the rotation hub so that the cap and the rotation hub are fixed to one another, wherein depressing a proximal portion of the wings extends the distal ends so that the wings are unlocked from the first flange.

In an embodiment, the advancement mechanism is loaded by locking the wings onto the first flange, thereby pushing the washer a third predetermined distance into the end cap and compressing the first and second springs, and releasing the cap so that the first spring pushes the washer back against the deformable tabs and the rotation hub proximally by the third distance while the second spring remains compressed between the washer and the second flange.

In an embodiment, the loaded advancement mechanism is unloaded by unlocking the wings from the first flange, causing the second spring to force the second flange of the rotation hub distally relative to the cap.

In an embodiment, the device further includes a cap fixed to the puncturing element; and a rotation hub fixed to the access cannula. Coupling the cap to the rotation hub at a proximal end of the handle automatically loads the advancement mechanism.

In an embodiment, the advancement mechanism is unloaded by unlocking the cap from the rotation hub.

In an embodiment, the device further includes a cap fixed to the puncturing element; and a rotation hub fixed to the access cannula, the rotation hub having a living hinge that, in an extended position, resists longitudinal motion of the rotation hub relative to the handle body, the living hinge being depressible into a depressed position by a mechanism in the cap so that the rotation hub may move longitudinally relative to the handle body.

In an embodiment, the device further includes a spring loaded against the rotation hub when the living hinge is in the extended position, wherein depressing the living hinge unloads the spring and moves the rotation hub a predetermined distance relative to the handle body. The present disclosure also relates to a device which includes an access cannula including a lumen extending therethrough, the access cannula being sized and shaped to extend through an endoscopic shaft to a target tissue within a living body; a puncturing element sized and shaped to extend through the lumen of the access cannula and distally out a distal end of the access cannula; and a handle including a handle body, a rotation hub fixed to the access cannula and a cap fixed to the puncturing element, the handle including a mechanism for advancing the rotation hub from a proximal position to a distal position relative to the handle body while the cap remains substantially stationary relative to the handle body.

The present disclosure also relates to a system which includes an endoscope including an endoscopic shaft; an access cannula including a lumen extending therethrough, the access cannula being sized and shaped to extend through the endoscopic shaft to a target tissue within a living body; a puncturing element sized and shaped to extend through the lumen of the access cannula and distally out a distal end of the access cannula; and a handle including a handle body, a rotation hub fixed to the access cannula and a cap fixed to the puncturing element, the handle including a mechanism for advancing the rotation hub from a proximal position to a distal position relative to the handle body while the cap remains substantially stationary relative to the handle body.

In addition, the present invention relates to a method. The method includes advancing an access cannula through an endoscopic shaft to a target tissue within a living body, the access cannula including a lumen extending therethrough; advancing a puncturing element through the lumen of the access cannula so that a puncturing tip of the puncturing element extends distally out a distal end of the access cannula, a cap being fixed to a proximal end of the puncturing element; coupling the cap to a proximal end of a handle; and actuating a mechanism in the handle to advance the access cannula from a proximal position relative to the puncturing element, where the puncturing tip is exposed distal to the distal end of the access cannula, to a distal position relative to the puncturing element, where the distal end of the access cannula covers the puncturing tip of the puncturing element.

In an embodiment, in the proximal position, the puncturing tip extends a first predetermined distance relative to the distal end of the access cannula and, when the advancement mechanism is actuated, the access cannula advances at least the first predetermined distance relative to the puncturing element.

In an embodiment the proximal end of the handle comprises a rotation hub coupled to a handle body, the rotation hub being fixed to the access cannula, rotatable relative to the handle body and slidable a second predetermined distance relative to the handle.

In an embodiment, the cap is coupled to the rotation hub and the coupling automatically loads the advancement mechanism.

In an embodiment, the method further includes unloading the advancement mechanism by unlocking the cap from the rotation hub.

BRIEF DESCRIPTION

DETAILED DESCRIPTION OF THE DRAWINGS

The present disclosure may be understood with reference to the following description and the appended drawings, wherein like elements are referred to with the same reference numerals. The exemplary embodiments describe endoscopic access devices with features for advancing an access cannula distally relative to the sharp puncturing tip ("sharp") when the clinician is ready to withdraw the sharp, i.e. after a puncture has been completed, to reduce the potential for an inadequate puncture depth and loss of access to the puncture hole.

Figure 1:
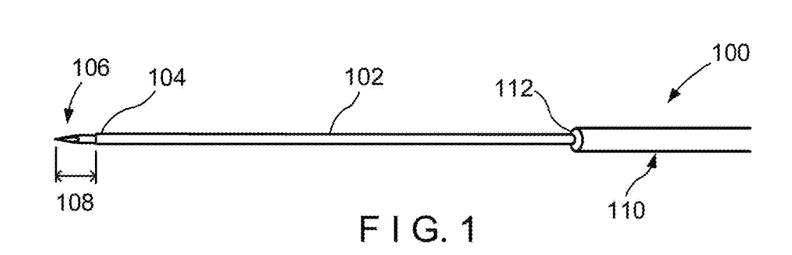
FIG. 1 shows a distal aspect of an endoscopic access device in a puncturing configuration according to various exemplary embodiments described herein.

FIG. 1 shows a distal aspect of an endoscopic access device 100 according to various exemplary embodiments described herein. The access device 100 includes an access cannula 102 with a flexible distal tip 104 biased to assume, when unconstrained, a J-shape (J-tip). A sharp 106 with a pointed tip (i.e., a puncturing element) is advanced through the lumen of the access cannula 102 so that the flexible J-tip 104 is straightened via the stiffness of the sharp 106 until the sharp 106 extends distally out the distal end of the J-tip 104 by a predetermined distance so that the sharp 106 may be used to puncture target tissue and the sharp 106 and J-tip 104 may be advanced together into the target anatomy.

Figure 2:
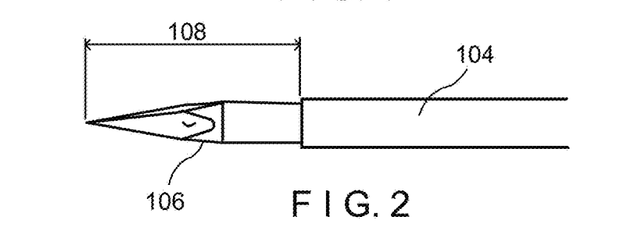
FIG. 2 shows a magnified view of the distal end of the endoscopic access device shown in FIG. 1.

A distance 108 by which the distal tip of the sharp 106 protrudes distally beyond the distal end of the J-tip 104 when the sharp 106 is inserted therein is referred to as the "setback," as shown in FIG. 2. The length of the sharp 106 and the length of the access cannula 102 are designed so that, when the sharp 106 is fully inserted in the handle and a rotation hub 202 at the proximal end of the device 100 is in a proximal (loaded) position, to be explained in further detail below, the setback 108 is a desired length for performing the initial puncturing of the access procedure.

Figure 3:
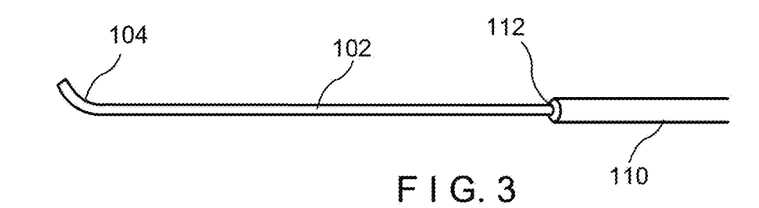
FIG. 3 shows the distal aspect of the endoscopic access device shown in FIG. 1 with the sharp withdrawn.

After the J-tip 104 and the sharp 106 have been advanced into the target anatomy as desired, the sharp 106 is withdrawn proximally out of the J-tip 104, freeing the J-tip 104 to return to its curved J-shape, as shown in FIG. 3. A guidewire may then be inserted through the lumen of the access cannula 102 and out of the distal end of the J-tip 104 into the target anatomy in a desired direction determined based on the aiming of the curved end of the J-tip 104. For example, before the guidewire is inserted into the access cannula 102, the J-tip 104 may be rotated via the rotation hub 202 to point a distal opening of the J-tip 104 in a desired direction within the target anatomy as would be understood by those skilled in the art.

Where the target anatomy is a bile duct, the J-tip 104 may be rotated so that the distal opening of the lumen of the access cannula 102 faces either upstream in the bile duct or downstream toward an outlet of the bile duct into the small intestine. When the J-tip 104 is oriented as desired, the guidewire is passed through the access cannula 102 to exit the opening at the distal end of the J-tip 104 until it extends a desired out of the J-tip 104 in the desired direction along the bile duct. At this point, a flexible electrosurgical sheath 110 with an electrosurgical tip 112 may be advanced over the access cannula 102 and the J-tip 104 to dilate a first hole by which the access cannula 102 exited the small intestine and a second hole by which the access cannula 102 entered the target bile duct. As would be understood by those skilled in the art, an electrode of the electrosurgical tip 112 may be activated when the tip 112 is located at the entrance to and within either or both of the first and second holes to cut and widen the holes to facilitate access to the target anatomy for further procedures (e.g., placing a stent therein to bypass a blockage).

The sharp 106 is typically used to make a starter hole in the anatomy through which the wider diameter distal tip 104 (J-tip) of the access cannula 102 may be pushed so that, when the sharp 106 is removed, the J-tip 104 is firmly inserted through the puncture hole to a target position within the target anatomy. However, various complications may arise when performing this operation. For example, a physician viewing the puncturing via ultrasound or fluoroscopy may be unable to discern the location of the tip of the access cannula 102. Thus, the access cannula 102 may not be inserted sufficiently deeply into the anatomy to maintain access when the sharp 106 is removed. In another example, the withdrawal of the sharp 106 may provide a proximal pull to the access cannula 102 that disengages the J-tip 104 from the puncture hole.

Figure 4:
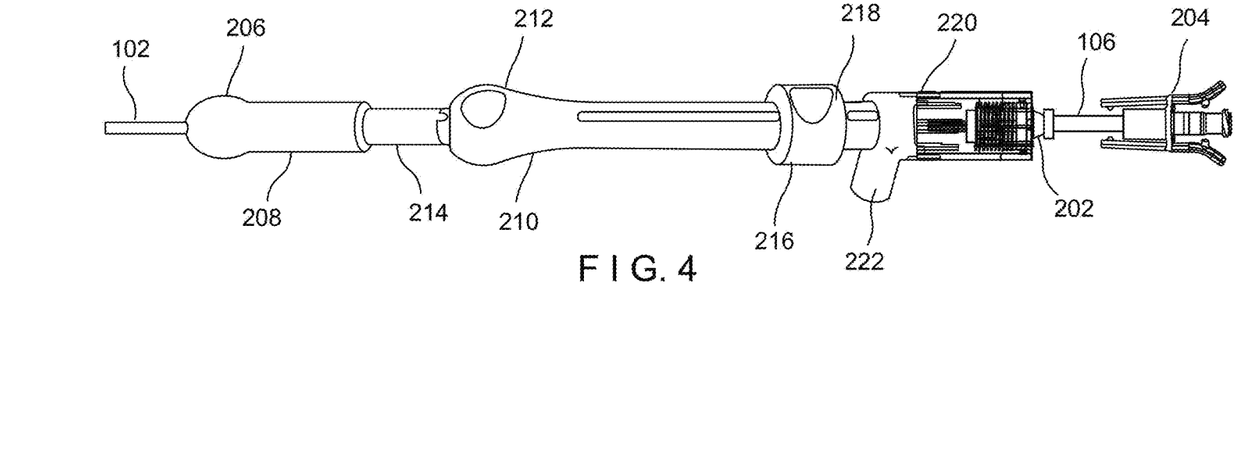
FIG. 4 shows a handle of the endoscopic access device of FIG. 1 for controlling an access procedure according to a first exemplary embodiment.

FIG. 4 shows a handle 200 of the endoscopic access device 100 for controlling an access procedure according to a first exemplary embodiment. A proximal end of the handle 200 includes the rotation hub 202 and a removable sharp cap 204. The access cannula 102 of this embodiment is rigidly fixed to the rotation hub 202 and extends through the interior of the handle 200 and out the distal end thereof. The rotation hub 202 has a channel extending therethrough providing access to the lumen of the access cannula 102 from a proximal end of the rotation hub 202, specifically for the sharp 106 to be inserted therein and extended through the length of the access cannula 102.

The sharp 106 of this embodiment is rigidly fixed to the sharp cap 204 so that advancing the sharp cap 204 distally advances the sharp 106 distally relative to the access cannula 102 and drawing the sharp cap 204 proximally withdraws the sharp 106 proximally relative to the access cannula 102. The sharp cap 204 couples to the proximal end of the handle 200 and, when the sharp cap 204 is so coupled, the sharp 106 may be extended to its most distal position. When coupled, the sharp cap 204 is positioned radially around the rotation hub 202. The sharp cap 204 is shown in FIG. 4 in a partially withdrawn position relative to the handle 200 and the access cannula 102. The proximal aspects of the handle 200, including the rotation hub 202 and the sharp cap 204, will be described in greater detail below with regard to the access cannula advancement mechanism.

The handle 200 has a distal collar 206 that attaches to a coupling at a proximal end of an endoscope shaft. The handle 200 includes a length adjust 208 via which a user can adjust a length of the handle 200 so that, when coupled to an endoscope, a length of the electrosurgical sheath 110 will extend a desired distance distally beyond a distal end of the endoscope (i.e., the length adjust may be used to achieve a desired extension of the device out the endoscope). The handle 200 further includes a puncture actuator 210 that is slidable over a base 214 of the handle 200 so that, when unlocked via a puncture actuator lock 212, the access cannula 102 and the sharp 106 are advanced distally out of the electrosurgical sheath 110 so that the J-tip 104 and the sharp 106 can penetrate target tissue to a desired depth.

The handle 200 further includes an electrosurgical sled 216 slidably mounted over the puncture actuator 210, the sled 216 being coupled to the electrosurgical sheath 110. The sheath 110 extends distally through the handle 200 from the sled 216 so that the sheath 110 can be advanced distally from an initial proximal position over the access cannula 102 to bring the electrosurgical tip 112 at the distal end of the sheath 110 into contact with target tissue so that the tissue may be treated by the application of energy from the tip 112 (e.g., to cauterize tissue around an opening formed through a wall of the gastrointestinal tract and an entry opening into a target pancreatico-biliary lumen).

The handle 200 includes a generator connection 222 extending therefrom at which a source of electrical energy may be coupled to the device 100, specifically to the electrosurgical sheath 110, and an end cap 220. The electrosurgical sled 216 is maintained in a desired position over the puncture actuator 210 via an electrosurgical sled lock 218. Depressing the sled lock 218 permits the electrosurgical sled 216 to slide over the puncture actuator 210.

Figure 5:
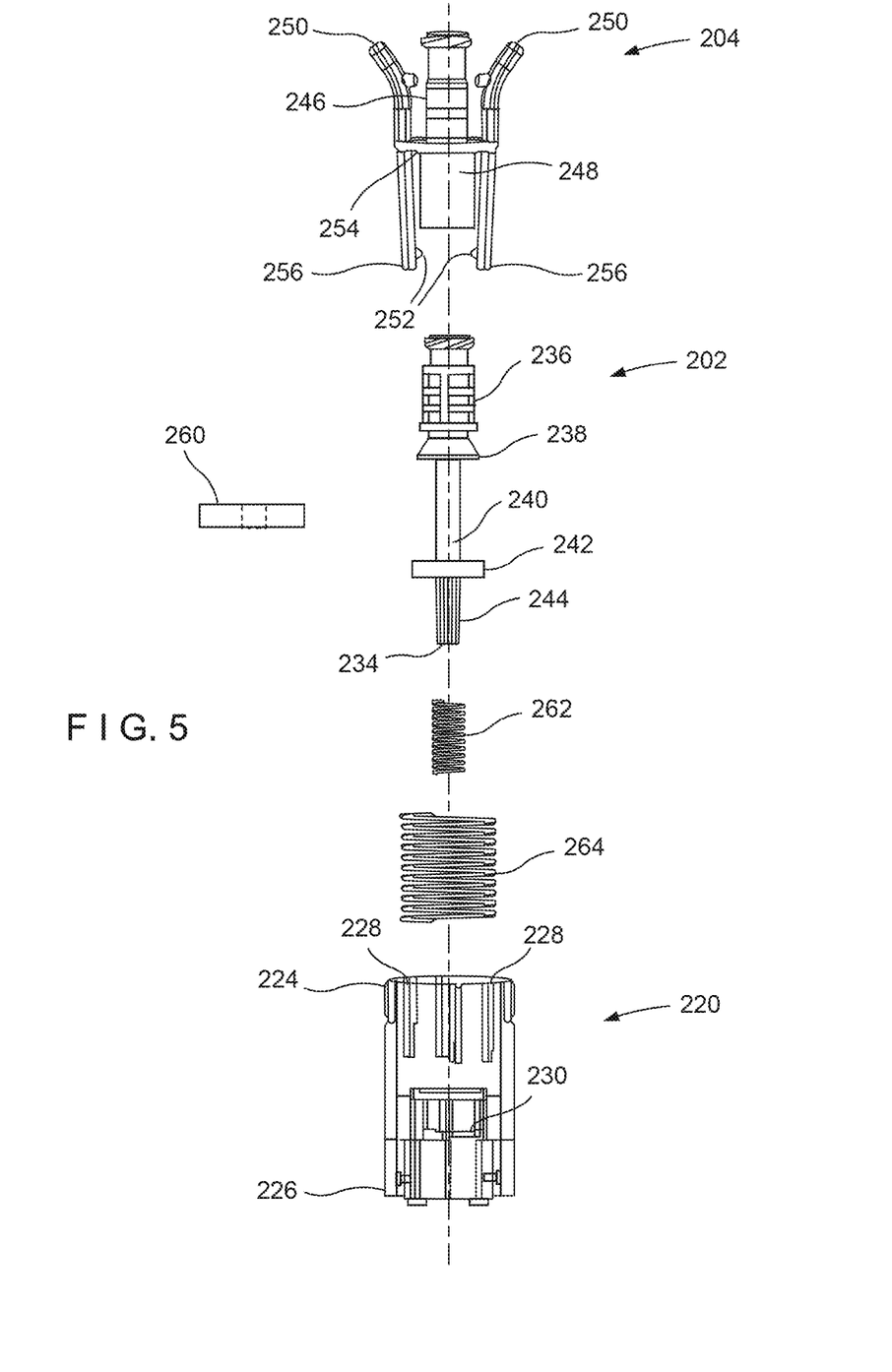
FIG. 5 shows an exploded view of the proximal end of the handle of FIG. 4.

FIG. 5 shows an exploded view of the proximal end of the handle 200 including an access cannula advancement mechanism to maintain a depth of puncture for the access cannula 102 during removal of the sharp 106. FIGS. 6-13 show views of the proximal end of the handle 200 at varying stages of assembly and deployment of the advancement mechanism. The handle 200 includes an end cap spring 264 and a rotation hub spring 262 for loading and deploying the advancement mechanism, to be explained in greater detail below.

The end cap 220 has a distal end 226 that couples to a proximal end of the handle 200 and an open proximal end 224 for receiving a distal portion of the rotation hub 202 therein. The end cap 220 is cannulated so that the rotation hub 202 and the access cannula 102 may extend therethrough. The proximal end 224 of the end cap 220 has two or more deformable tabs 228 extending radially inward, seen more clearly in FIG. 9, to keep a washer 260 in place within the end cap 220 when the proximal end of the handle 200 is assembled. The inner surface of the end cap 220 reduces in size from a greater diameter proximal portion to a reduced diameter distal portion, the reduction in size forming a seat 230 against which the end cap spring 264 is loaded, to be explained further below.

The rotation hub 202 extends from a proximal end 232 coupling to the sharp cap 204 to a distal end 234 which couples in turn to the end cap 220. The rotation hub 202 includes a proximal portion 236 with an outer diameter sized and shaped to be received within a distal portion 248 of the sharp cap 204. A first flange 238 with a flared conical shape extends distally from the proximal portion 236 for locking the sharp cap 204 thereto, to be explained further below. A shaft 240 extends from the first flange 238 to a second flange 242, and a fluted distal portion 244 extends from the second flange 242 to the distal end 234 for locking the rotation hub 202 in a temporarily fixed position relative to the handle 200. The flutes of the distal portion 244 engage aspects of the interior of the handle 200 that provide resistance to rotation of the rotation hub 202, but may be overcome by a sufficient force so that the rotation hub 202 may be rotated in increments and remain temporarily locked into a position pending further rotation.

Figure 11:
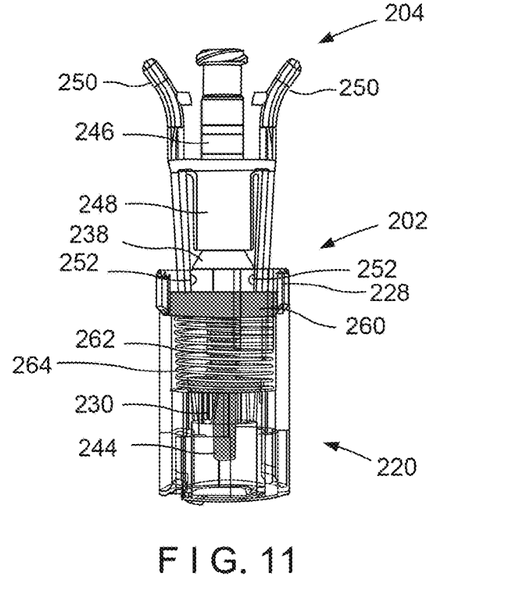
Figure 12:
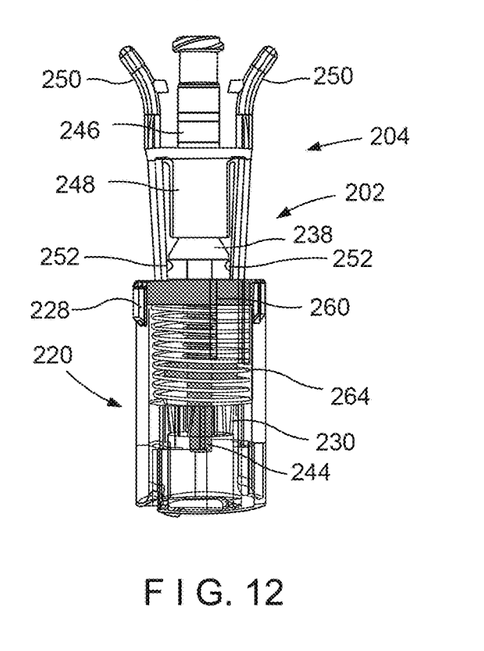

The sharp cap 204 has a proximal portion 246 that may be gripped by an operating physician. The sharp 106 extends from an interior of the proximal portion 246 through a hollow distal portion 248 that is extended over the proximal portion 236 of the rotation hub 202 when the sharp cap 204 is coupled thereto. A flanged portion 254 having a greater diameter connects the proximal and distal portions 246, 248 and two wings 250 are connected to the flanged portion 254 for locking the sharp cap 204 to and unlocking the sharp cap 204 from the rotation hub 202. The wings 250 extend from a proximal end to a distal end 256 and are attached at a medial location thereon to the flanged portion 254 so that a proximal portion of each of the wings 250 may be depressed, i.e. pushed radially inward, to widen a distal portion. The distal portion of each wing 250 has a bump 252 projecting radially inward that locks onto the first flange 238 of the rotation hub 202, as seen in FIGS. 11-12, to couple the sharp cap 204 to the rotation hub 202. Depressing the proximal ends of the wings 250 widens the distal ends to unlock the sharp cap 204 from the rotation hub 202 and, when the advancement mechanism is loaded, simultaneously releases the rotation hub 202 to advance the J-tip 104 over the distal end of the sharp 106.

The advancement mechanism includes the washer 260 disposed about the shaft 240 of the rotation hub 202, i.e., between the first and second flanges 238, 242, and slidable relative thereto. The rotation hub spring 262 is also disposed between the first and second flanges 238, 242, specifically between the washer 260 and the second flange 242 so that the rotation hub spring 262 may be compressed by sliding the washer 260 distally over the shaft 260. The end cap spring 264 is positioned inside the end cap 220 against the seat 230. While the rotation hub spring 262 has a smaller diameter, so that the rotation hub spring 262 is contained on the shaft 240 by the second flange 242, the end cap spring 264 has a greater diameter so that the second flange 242 may be inserted within the end cap spring 264 without interfering therewith. The end cap spring 264 may be compressed by the washer 260 against the seat 230 in the manner described below.

Figure 6:
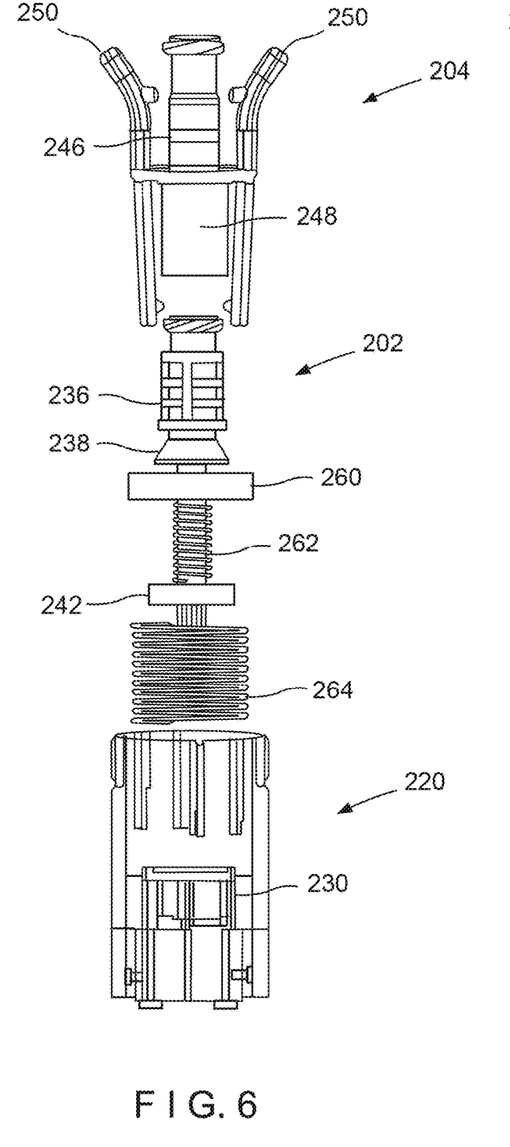
FIGS. 6-13 show views of the proximal end of the handle of FIG. 4 at varying stages of assembly and deployment of the access cannula advancement mechanism.
Figure 7:
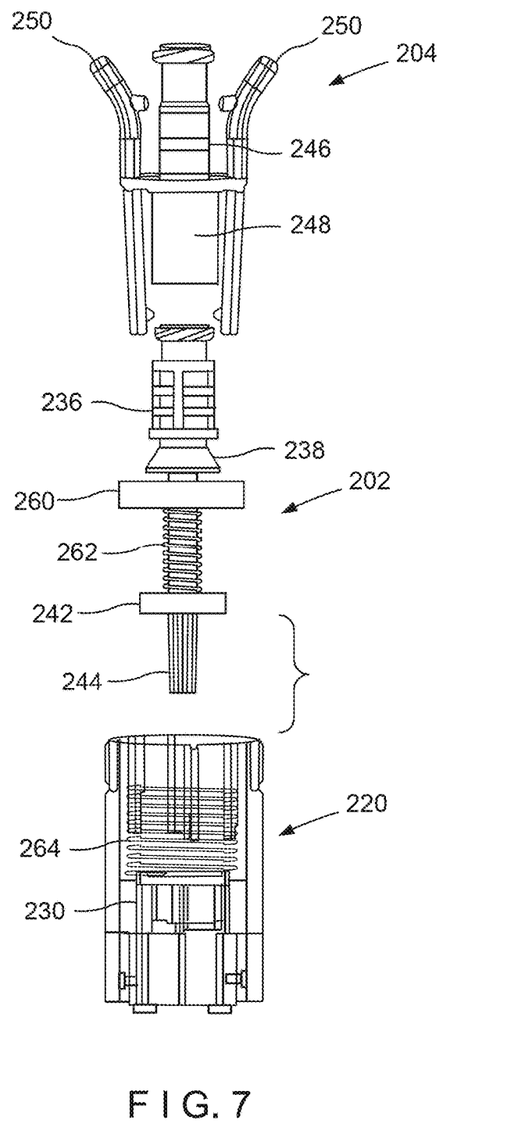
Figure 8:
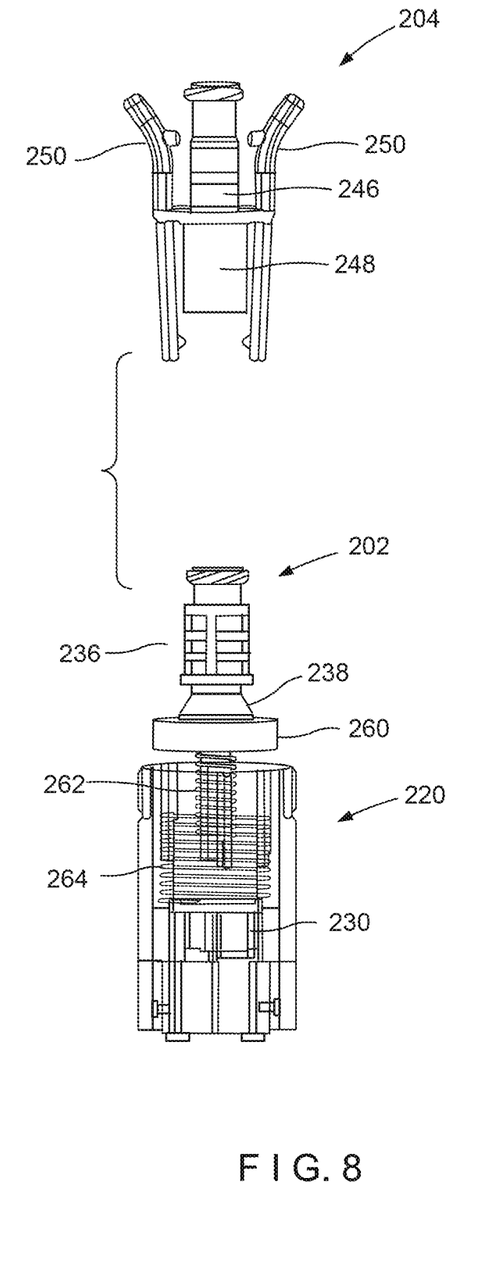
Figure 9:
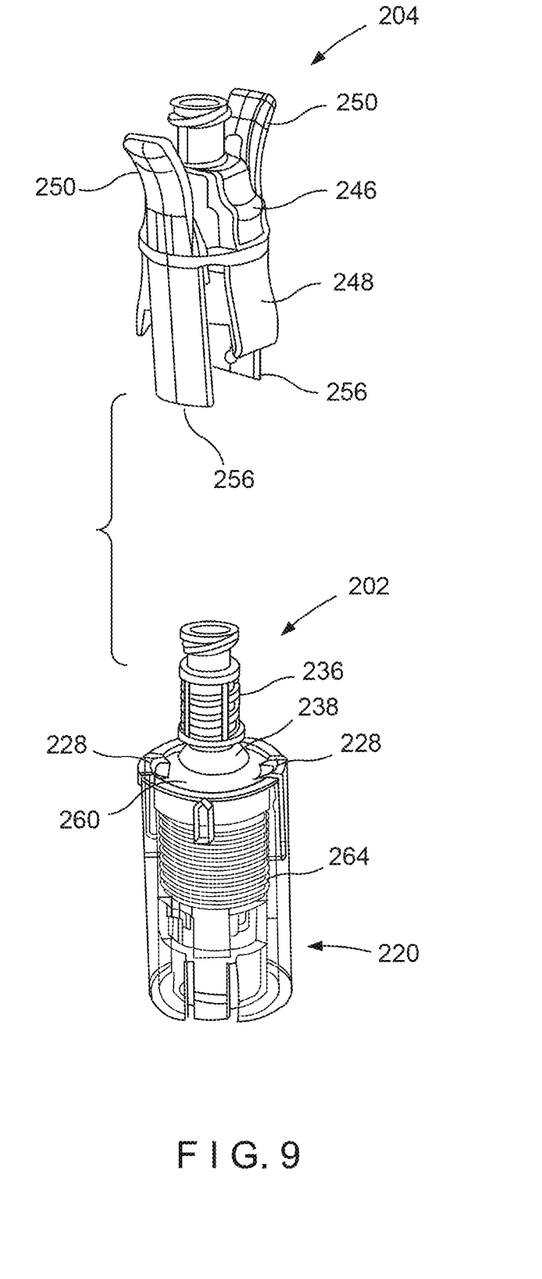

FIGS. 6-13 show views of the proximal end of the handle 200 at varying stages of assembly and deployment of the advancement mechanism. FIG. 6 shows the arrangement of the washer 260 and the rotation hub spring 262 relative to the rotation hub 202, while FIG. 7 shows the end cap spring 264 arranged within the end cap 220 against the seat 230. FIG. 8 shows the rotation hub 202 being inserted into the end cap 220. FIG. 9 shows a perspective view of the proximal end of the handle 200 with the rotation hub 202 fully inserted in the end cap 220. The deformable tabs 228 allow for the washer 260 to be pressed into the end cap 220, but are shaped to keep the washer 260 within the end cap 220, even when a force is applied proximally on the washer 260, i.e. when the end cap spring 264 is compressed against the washer 260. It is noted that the access cannula advancement mechanism is not yet loaded when the proximal end of the handle 200 is arranged in the manner shown in FIG. 9.

Figure 10:
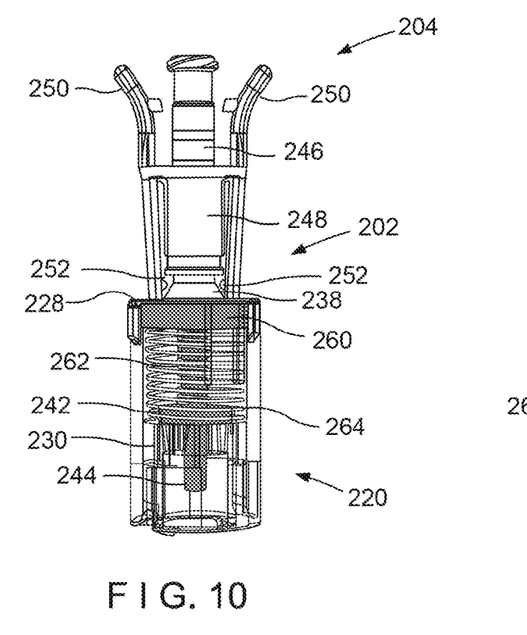
Figure 13:
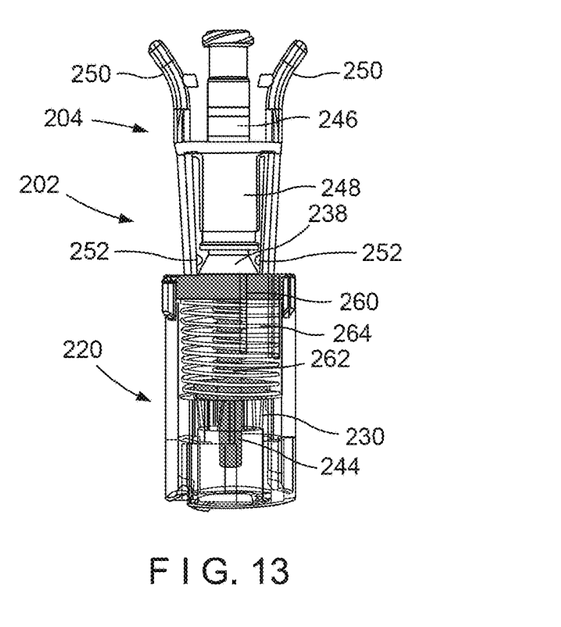
Figure 14:
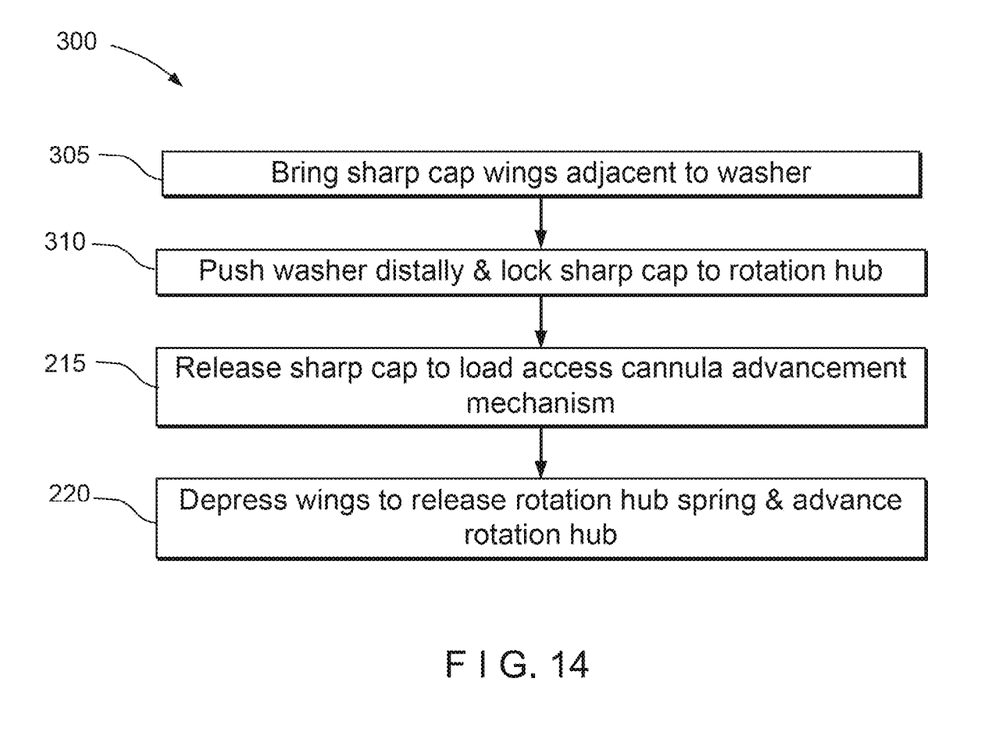
FIG. 14 shows a method for loading and deploying the access cannula advancement mechanism.

The loading and deployment of the advancement mechanism is shown in FIGS. 10-13 and will be described with the method 300 shown in FIG. 14. The advancement mechanism is loaded simultaneously with the coupling of the sharp cap 204 to the rotation hub 202. In 305, the sharp 106 is introduced into the access cannula 102 and advanced distally so that the sharp cap 204 is advanced distally onto the handle 200, specifically over the rotation hub 202, until the distal ends 256 of the wings 250 are adjacent to the washer 260, as shown in FIG. 10. In this position, the distal tip of the sharp 106 is within the J-tip 104, i.e., not exposed distally to the J-tip 104.

In 310, the sharp cap 204 is pushed further distally over the rotation hub 202 so that the distal ends 256 of the wings 250 push the washer 260 distally, as shown in FIG. 11. Several actions occur simultaneously during this step. The advancement of the sharp cap 204 relative to the rotation hub 202 pushes the distal tip of the sharp 106 out of the distal end of the access cannula 102 so that the sharp 106 may be used to puncture the target anatomy during an access procedure. This advancement additionally brings the bumps 252 on the wings 250 past the first flange 238 of the rotation hub 202 to lock the sharp cap 204 with the rotation hub 202. The location of the bumps 252 on the wings 250 is configured relative to the distal ends 256 of the wings so that the washer 260 is held a predetermined distance from the first flange 238 of the rotation hub 202. The pushing of the washer 260 compresses both the rotation hub spring 262 (against the second flange 242 of the rotation hub 202) and the end cap spring 264 (against the seat 230 of the end cap 220).

In 315, the sharp cap 204 is released, allowing the end cap spring 264 to push the washer 260 proximally back to its initial position against tabs 228 of the end cap 220, as shown in FIG. 12. However, because of the locked configuration of the sharp cap 204 and the rotation hub 202, both the sharp cap 204 and the rotation hub 202 are pushed proximally with the end cap spring 264. In this state, the rotation hub spring 262 is compressed and loaded. The operating physician may perform the puncturing of the target anatomy using the sharp 106, which is extended out of the access cannula 102. When the target anatomy is accessed to an adequate depth, and the physician is ready to withdraw the sharp, the method advances to 320.

In 320, the proximal ends of the wings 250 of the sharp cap 204 are depressed, i.e. pushed radially inward, to move the distal ends 256 of the wings 250, more particularly the bumps 252, radially outward to release the sharp cap 204 from the rotation hub 202 and allow the rotation hub spring 262 to decompress. Because the washer 260 is at its most proximal position, and cannot be forced further proximally from the force of the spring 262, the decompression of the spring 262 instead applies a force to the second flange 242 of the rotation hub 202 and forces the rotation hub 202 distally relative to the sharp cap 204, as shown in FIG. 13. This brings the sharp cap 204 and the rotation hub 202 back to their initial positions, i.e. the positions shown in FIG. 10.

At this point, the J-tip 104 of the access cannula 102 has been forced over the tip of the sharp 106 without changing the position of the sharp 106. During the access procedure, this motion further entrenches the access cannula 102 in the puncture hole created by the sharp 106. The sharp cap 204 is unlocked from the rotation hub 202, thus the sharp cap 204 may be withdrawn proximally, drawing the sharp 106 proximally. The J-tip 104 reverts to its J-shaped configuration, and the sharp 106 is ultimately removed from the handle 200 so that the access cannula 102 may be used for further aspects of the procedure, e.g. inserting a guidewire.

Figure 15:
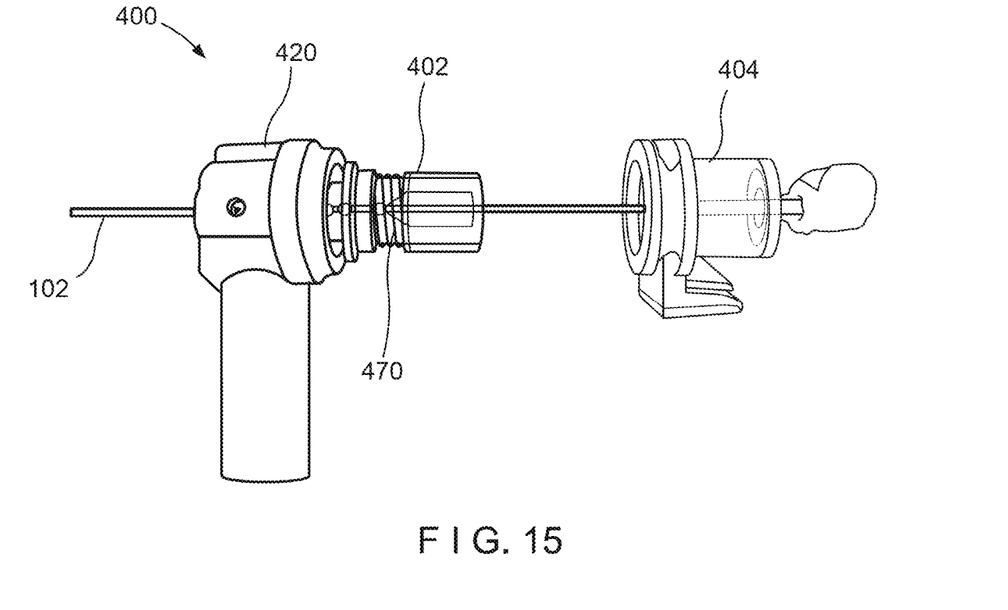
FIG. 15 shows a partially disassembled view of a proximal end of a handle for controlling an access procedure according to a second exemplary embodiment.

FIG. 15 shows a partially disassembled view of a distal end of a handle 400 according to a second exemplary embodiment. The handle 400 is substantially similar to the handle 200 described above, however with a rotation hub 402, a sharp cap 404 and an end cap 420 replacing the rotation hub 202, sharp cap 204, and end cap 220 described above. The access cannula 102, sharp 106 and electrosurgical sheath 110 described in FIGS. 1-3 may be used with the handle 400. The second embodiment includes a spring 470 that is loaded against the rotation hub 402 and may be released to force the rotation hub 402 distally.

Figure 16:
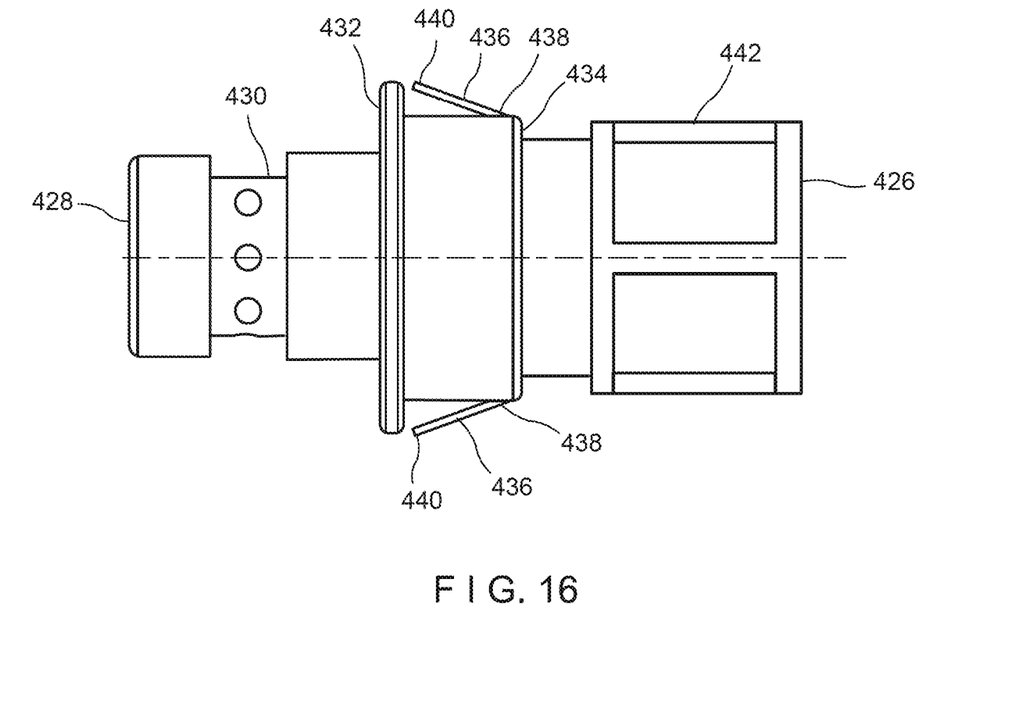
FIG. 16 shows the rotation hub of the proximal end of the handle shown in FIG. 15.

The rotation hub 402, seen in greater detail in FIG. 16, extends from a proximal end 426 to a distal end 428 and has a distal portion 430 slidably coupling to an inner surface of the end cap 420. The distal portion 430 is sized so that its diameter substantially corresponds to that of the interior of the end cap 420 and, absent any applied forces, the rotation hub 402 remains in a fixed position relative to the handle 400. However, the distal portion 430 and the end cap 420 are fit loosely enough so that a rotational force on the rotation hub 402 allows rotation of the hub 402 relative to the handle 400 and translates to rotation of the access cannula 102 and its J-tip 104.

The distal portion 430 of the rotation hub 402 is also slidable longitudinally relative to the end cap 420, translating to longitudinal advancement or retraction of the access cannula 102 relative to stationary device components. The access cannula advancement mechanism for the handle 400, to be explained in further detail below, slides the rotation hub 402 distally from an initial proximal position to a distal position while the sharp cap 404 remains in fixed position, thus advancing the access cannula 102 deeper into the target tissue over the sharp 106 during an access procedure, similar to the advancement mechanism described above for the handle 200. The advancement mechanism may be actuated just prior to releasing the sharp cap 404 from the handle 400 for withdrawal of the sharp 106.

The rotation hub 402 has a flange portion 432 having a diameter greater than that of the distal portion 430, and thus greater than that of the inner surface of the end cap 420 where the distal portion 430 couples to the end cap 420, so that the flange 432 may not advance distally past the proximal end of this inner surface of the end cap 420. A medial portion 434 of the rotation hub 402 has two living hinges 436 extending distally and radially outward from first ends 438 to second ends 440. The living hinges 436 are disposed on opposite sides of the medial portion 434.

When the rotation hub 402 is in its proximal (i.e. loaded) position the second ends 440 of the hinges 436 abut the proximal end of the end cap 420, preventing distal motion of the rotation hub 402 relative thereto. The living hinges 436 are depressed to allow a preloaded single or double spring 470, as shown in FIG. 15 but omitted in FIG. 16, to advance the rotation hub 402 to its distal (i.e. unloaded) position, in a manner to be explained below. A proximal portion 442 of the rotation hub 402 is received in the sharp cap 404 when the components are coupled.

Figure 17:
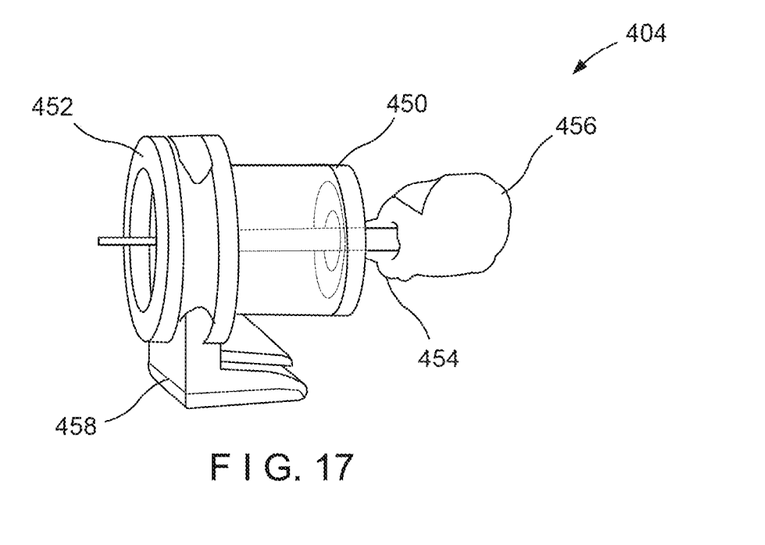
FIG. 17 shows the sharp cap of the proximal end of the handle shown in FIG. 15.

The sharp cap 404, seen in greater detail in FIG. 17, is substantially hollow, having a cylindrical interior extending therethrough from a substantially closed proximal end 450 to an open distal end 452. The proximal end 450 has a hole for a sharp sheath 454 to extend through, the sharp sheath 454 being fixed to the cap 404 and to the sharp 106 and having a proximal end proximal to the sharp cap 404 with a grip 456 for manually advancing and retracting the sharp cap 404 and the rigidly fixed sharp 106 relative to stationary device components. The sharp cap 404 is slid over the rotation hub 402 to assemble the device in preparation for puncturing target tissue. In the assembled configuration, the distal end 452 is positioned over the living hinges 436 of the rotation hub 402.

The sharp cap 404 has a lock release 458 extending through its diameter adjacent to its distal end 452. When the sharp cap 404 and the rotation hub 402 are assembled the lock release 458 is positioned over the living hinge 436. Pressing the lock release 458 causes an inner portion thereof to depress the living hinge 436, bringing the second end 440 of the hinge 436 out of contact with the end cap 420 and allowing the rotation hub 402 to slide distally relative thereto.

The rotation hub 402 has a spring 470 connected to the flange 432 and loaded against the sharp cap 404 when the components are assembled. When the lock release 458 is pushed, the hinges 436 are depressed and the spring 470 is allowed to unload and advance the rotation hub 402, and the access cannula 102, distally a predetermined distance relative to the sharp 106, which remains in a fixed position. Thus, the distal J-tip 104 is pushed over the sharp 106 and maintains access to the target anatomy when the sharp 106 is subsequently removed.

Figure 18A:
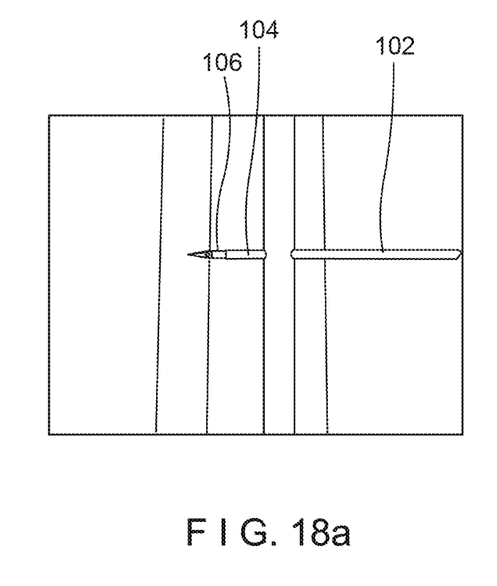
FIG. 18a shows the distal end of the endoscopic access device shown in FIG. 1 in an initial puncturing configuration.
Figure 18B:
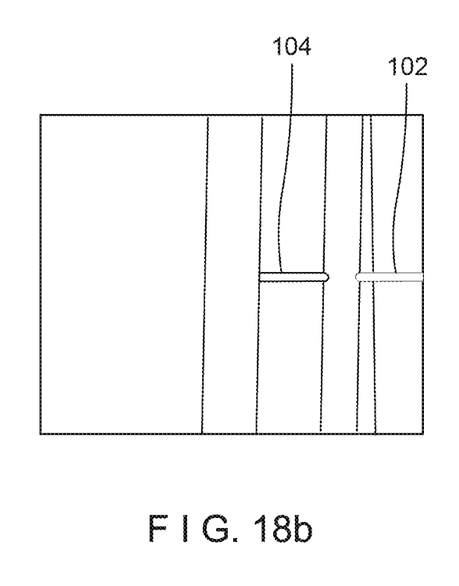
FIG. 18b shows the distal end of the endoscopic access device shown in FIG. 1 in a post-puncturing configuration.

FIG. 18a shows the distal end of the device according to either of the first or second embodiments when the devices are in the loaded position and the sharp 106 is extended in a puncturing configuration. FIG. 18b shows the distal end of the device according to either of the first or second embodiments when the devices are in the unloaded position and the access cannula is advanced over the distal tip of the sharp 106.

In a third embodiment, the device handle includes a sliding component that may be advanced manually to bring the access cannula over the sharp tip prior to sharp removal, rather than utilizing an automatic spring-loaded advancement mechanism as described above. The sliding component may be rigidly fixed to the rotation hub so that sliding the sliding component longitudinally also moves the rotation hub longitudinally relative to the sharp. The sliding component is slidable between a proximal position, where the sharp is exposed for puncturing, and a distal position, where the sharp is covered. The sliding component is held in either of the two positions via friction or snaps.

In a fourth embodiment, the device handle includes a rack and pinion gear arrangement. The handle includes a rack attached to the access cannula. A gear is coupled to the rack and has a shaft extending through its center and through both sides of the handle, to which it is positionally fixed but allowed to rotate relative thereto. An advancement hub is on one of the two ends of the shaft, and turning the advancement hub rotates the gear, which engages the rack and pushes the access cannula proximally or distally, depending on the direction of rotation.

In a fifth embodiment, a two-position lever attached to the rotation hub is used to implement the distal/proximal movement described in the previous embodiments.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

The invention claimed is:

1. A method, comprising:
    advancing an access cannula through an endoscopic shaft to a target tissue within a living body, the access cannula including a lumen extending therethrough;
    advancing a puncturing element through the lumen of the access cannula so that a puncturing tip of the puncturing element extends distally out a distal end of the access cannula, a cap being fixed to a proximal end of the puncturing element;
    coupling the cap to a proximal end of a handle, wherein the cap and the puncturing element are maintained in a fixed position relative to the handle; and
    actuating a mechanism in the handle to advance the access cannula from a proximal position relative to the puncturing element, where the puncturing tip is exposed distal to the distal end of the access cannula, to a distal position relative to the puncturing element, where the distal end of the access cannula covers the puncturing tip of the puncturing element;
    wherein, in the proximal position, the puncturing tip extends a first predetermined distance relative to the distal end of the access cannula and, when the advancement mechanism is actuated, the access cannula advances at least the first predetermined distance relative to the puncturing element;
    wherein the proximal end of the handle comprises:
        a rotation hub coupled to a handle body, the rotation hub being fixed to the access cannula, rotatable relative to the handle body and slidable a second predetermined distance relative to the handle; and
        an end cap into which a distal portion of the rotation hub is inserted to couple the rotation hub to the handle, the end cap including a seat against which a first spring is positioned,
            wherein the rotation hub includes a first proximal flange and a second distal flange with a shaft extending therebetween, the shaft having a washer and a second spring slidable thereover and constrained between the first and second flanges.

2. The method of claim 1, wherein the cap is coupled to the rotation hub and the coupling automatically loads the advancement mechanism.

3. The method of claim 2, further comprising:
    unloading the advancement mechanism by unlocking the cap from the rotation hub.

4. The method of claim 1, wherein the end cap further includes deformable tabs at a proximal end thereof that allow insertion of the washer therein and resist retraction of the washer thereout so that, when the rotation hub is inserted into the end cap, the washer is positioned against the first spring at a distal end and against the deformable tabs at a proximal end.

5. The method of claim 4, wherein the cap includes a distal portion sized and shaped to cover a proximal portion of the rotation hub and two wings attached thereto, each of the wings having a tab extending radially inward off of a distal end thereof.

6. The method of claim 5, wherein the cap is advanced over the rotation hub so that the tabs extend off the wings to lock onto the first proximal flange of the rotation hub so that the cap and the rotation hub are fixed to one another.

7. The method of claim 6, further comprising:
    depressing a proximal portion of the wings to extend the distal ends of the wings to unlock the wings from the first proximal flange.

8. The method of claim 7, further comprising:
    loading the advancement mechanism by locking the wings onto the first proximal flange, thereby pushing the washer a third predetermined distance into the end cap and compressing the first and second springs.

9. The method of claim 8, further comprising:
    releasing the cap so that the first spring pushes the washer back against the deformable tabs and the first spring pushes the rotation hub proximally by the third distance while the second spring remains compressed between the washer and the second flange.

10. The method of claim 9, further comprising:
    unloading the loaded advancement mechanism by unlocking the wings from the first flange, causing the second spring to force the second flange of the rotation hub distally relative to the cap.

11. The method of claim 1, wherein the rotation hub includes a living hinge that, in an extended position, resists longitudinal motion of the rotation hub relative to the handle body, the living hinge being depressible into a depressed position by a mechanism in the cap so that the rotation hub may move longitudinally relative to the handle body.

12. The method of claim 11, further comprising:
    loading a spring against the rotation hub when the living hinge is in the extended position, so that, depressing the living hinge unloads the spring and moves the rotation hub a predetermined distance relative to the handle body.

* * * * *